(12) United States Patent
Kolp et al.

(10) Patent No.: US 7,518,720 B2
(45) Date of Patent: Apr. 14, 2009

(54) OPTICAL FLOW CELL FOR USE IN HIGH TEMPERATURE AND/OR HIGH PRESSURE ENVIRONMENTS

(75) Inventors: Joseph P. Kolp, North Canton, OH (US); Thomas J. Sebok, Tallmadge, OH (US)

(73) Assignee: Lockheed Martin Corporation, Bethesda, MD (US)

( * ) Notice: Subject to any disclaimer, the term of this patent is extended or adjusted under 35 U.S.C. 154(b) by 14 days.

(21) Appl. No.: 11/888,565

(22) Filed: Aug. 1, 2007

(65) Prior Publication Data

US 2009/0031830 A1    Feb. 5, 2009

(51) Int. Cl.
  *G01N 21/01* (2006.01)
(52) U.S. Cl. .................................. 356/246; 356/244
(58) Field of Classification Search ................ 356/244, 356/246, 70–72, 440; 435/7.2, 287.2
  See application file for complete search history.

(56) References Cited

U.S. PATENT DOCUMENTS

| | | | | |
|---|---|---|---|---|
| 4,804,267 | A | 2/1989 | Greenfield | 356/335 |
| 4,872,753 | A | 10/1989 | Danigel et al. | 356/246 |
| 5,046,854 | A | 9/1991 | Weller et al. | 356/440 |
| 5,241,189 | A | 8/1993 | Vandagriff et al. | 250/575 |
| 5,594,544 | A | 1/1997 | Horiuchi et al. | 356/73 |
| 5,790,246 | A * | 8/1998 | Kuhnell et al. | 356/72 |
| 6,069,694 | A | 5/2000 | VonBargen | 356/246 |
| 6,104,483 | A | 8/2000 | Sebok et al. | 356/244 |
| 6,246,474 | B1 * | 6/2001 | Cerni et al. | 356/335 |
| 6,587,195 | B1 | 7/2003 | Jennings | 356/246 |
| 7,184,141 | B2 * | 2/2007 | Brewer et al. | 356/246 |
| 7,307,717 | B2 * | 12/2007 | Kolp et al. | 356/246 |
| 2004/0001200 | A1 | 1/2004 | Hirakawa et al. | 356/244 |
| 2004/0027568 | A1 | 2/2004 | Maiefski et al. | 356/326 |
| 2004/0189988 | A1 | 9/2004 | Scaduto | 356/244 |
| 2006/0044554 | A1 | 3/2006 | Mertz et al. | 356/246 |
| 2007/0064226 | A1 | 3/2007 | Kolp et al. | 356/246 |

FOREIGN PATENT DOCUMENTS

| | | |
|---|---|---|
| EP | 0 507 746 A2 | 3/1992 |
| WO | WO 95/12118 | 5/1995 |

\* cited by examiner

*Primary Examiner*—Sang Nguyen
(74) *Attorney, Agent, or Firm*—Renner Kenner Greive Bobak Taylor & Weber

(57) ABSTRACT

A flow cell for monitoring operating fluid in an environment with elevated temperature and/or pressure comprises a body having a body aperture. The body aperture provides opposing inlet and outlet flow slits that are disposed within a wall maintained by the body aperture. The body aperture is configured to receive upper and lower transparent plates that are separated by a pair of spaced shims. The spaced shims define a flow channel between the plates, which is aligned with the inlet and outlet flow slits. A retainer is attached by suitable fasteners to retain the plates and shims in place, and thus sealing the flow of operating fluid through the flow channel from the external environment.

21 Claims, 9 Drawing Sheets

OPTICAL FLOW CELL FOR USE IN HIGH TEMPERATURE AND/OR HIGH PRESSURE ENVIRONMENTS

TECHNICAL FIELD

Generally, the present invention relates to an optical flow cell for analyzing fluids. More specifically, the present invention relates to an online optical flow cell for analyzing fluids. Particularly, the present invention relates to an online optical flow cell that provides laminar flow of fluids through a flow channel, and which is able to withstand elevated environmental pressures and/or temperatures during its operation.

BACKGROUND ART

Operating fluids, including but not limited to lubricating fluid, hydraulic fluid, and liquid fuels, are used in various mechanical assemblies to perform a particular task. For example, lubricating fluid is used within a mechanical assembly to provide cooling and lubrication to the parts. Hydraulic fluid is pressurized by a pump to actuate a piston in order to generate a moving force. And liquid fuels provide a source of potential energy to various types of fuel driven engines. These fluids are generally used in mechanical assemblies where the fluids come in contact, or otherwise interact with, various supply lines, valves, reservoirs, pumps, and engines, as well as various other mechanical assemblies. As a result of this interaction, wear particles generated by moving parts within the machine as well as contamination particles from outside the machine are present in the fluid. These particles by themselves are not a problem for the machine because they are being removed by the oil filter. However, they are an indication of the type of wear going on within the machine. By knowing the type of wear particles being generated and their size, concentration and trend, a prediction on the health of the machine can be made. By knowing the health of the machine, servicing need only be done when it is required: saving time, money, and increasing the life of the machine.

For example, lubricating fluid, such as oil, used by an operating machine, such as a combustion engine, is often contaminated by the result of: combustion by-products, debris that has entered the air intake of the engine, and other particles that are the result of the wear of the internal parts of the engine. In particular, these particles, which are typically on the order of about 150 microns or less, are indicative of the overall wear of the engine. Moreover, by analyzing the physical characteristics, such as the size and shape of the particles in real-time, the current wear or "health" of the engine can be identified on an on-demand basis.

As a result, several systems that directly analyze the various operating fluids of an engine or other operating machine have been developed. One method, referred to as the "offline" method involves extracting a sample of operating fluid, and then sending the sample to a remotely located laboratory for analysis. Although this system is effective, it is time consuming as the analysis requires a substantial lead time from the time the sample is taken and until wear results are obtained.

Recently, fluid analysis systems have been developed, which utilize laser optical near-field imaging techniques. These systems comprise a laser light source, a light detection device, a flow cell, and a pump or other means to draw the fluid through the flow cell. One such type of flow cell utilizing near-field imaging techniques is disclosed in U.S. Pat. No. 6,104,483, which is incorporated herein by reference. This system determines the number of particles in the fluid, and then identifies the size and physical characteristics of the particle. Because the physical characteristics of a particle directly correspond to a particular wear mechanism or phenomena, the system can correlate the detected particle characteristics with the particular mechanism causing the wear, such as metal particles created by engine wear or debris entering through the air intake of an engine. As such, the system informs the user as to the source of the particles, thereby enabling the user to more accurately diagnose and remedy any engine problems that may exist.

Although the utilization of laser optical near-field imaging techniques provided by the flow cell have proven to be a significant advance in the prospect of real-time wear analysis, such systems are plagued by various limitations. For example, while manufacturers have overcome the technical obstacles associated with the operation of the flow cell at high temperature and/or high pressure, they have been unable to provide a flow cell that has a compact dimension, is lightweight, and cost effective, and which is able to maintain a laminar flow of the operating fluid therethrough. A laminar flow is advantageous in that it allows wear particles to pass uniformly through the flow cell, allowing a fluid analysis system to more accurately characterize the shape of the wear particles.

Therefore, there is a need in the art for an optical flow cell that is configured to provide laminar flow of the operating fluid passing therethrough. Moreover, there is a need in the art for an optical flow cell that is configured to withstand environments having high pressure and/or high temperature, while providing laminar flow to the operating fluid passing therethrough.

SUMMARY OF INVENTION

In light of the foregoing, it is a first aspect of the present invention to provide an optical flow cell for use in high temperature and/or high pressure environments.

It is another aspect of the present invention to provide a flow cell to monitor particles in a fluid comprising a body having a body aperture therethough forming a wall surface, a pair of slits disposed within opposing sides of the wall surface, wherein one of the slits receives an incoming flow of fluid, and the other slit receives an outgoing flow of fluid, a pair of spaced transparent plates disposed within the aperture, the space between the plates defining a flow channel substantially aligned with each of the slits allowing the fluid to pass therethrough in a laminar manner, and a retainer attached to the body to retain the plates in place, the retainer having a retainer aperture, wherein the body aperture, the flow channel, and the retainer aperture are substantially aligned to allow light to pass threrethrough.

BRIEF DESCRIPTION OF THE DRAWINGS

These and other features and advantages of the present invention will become better understood with regard to the following description, appended claims, and accompanying drawings wherein:

BEST MODE FOR CARRYING OUT THE INVENTION

Figure 1:
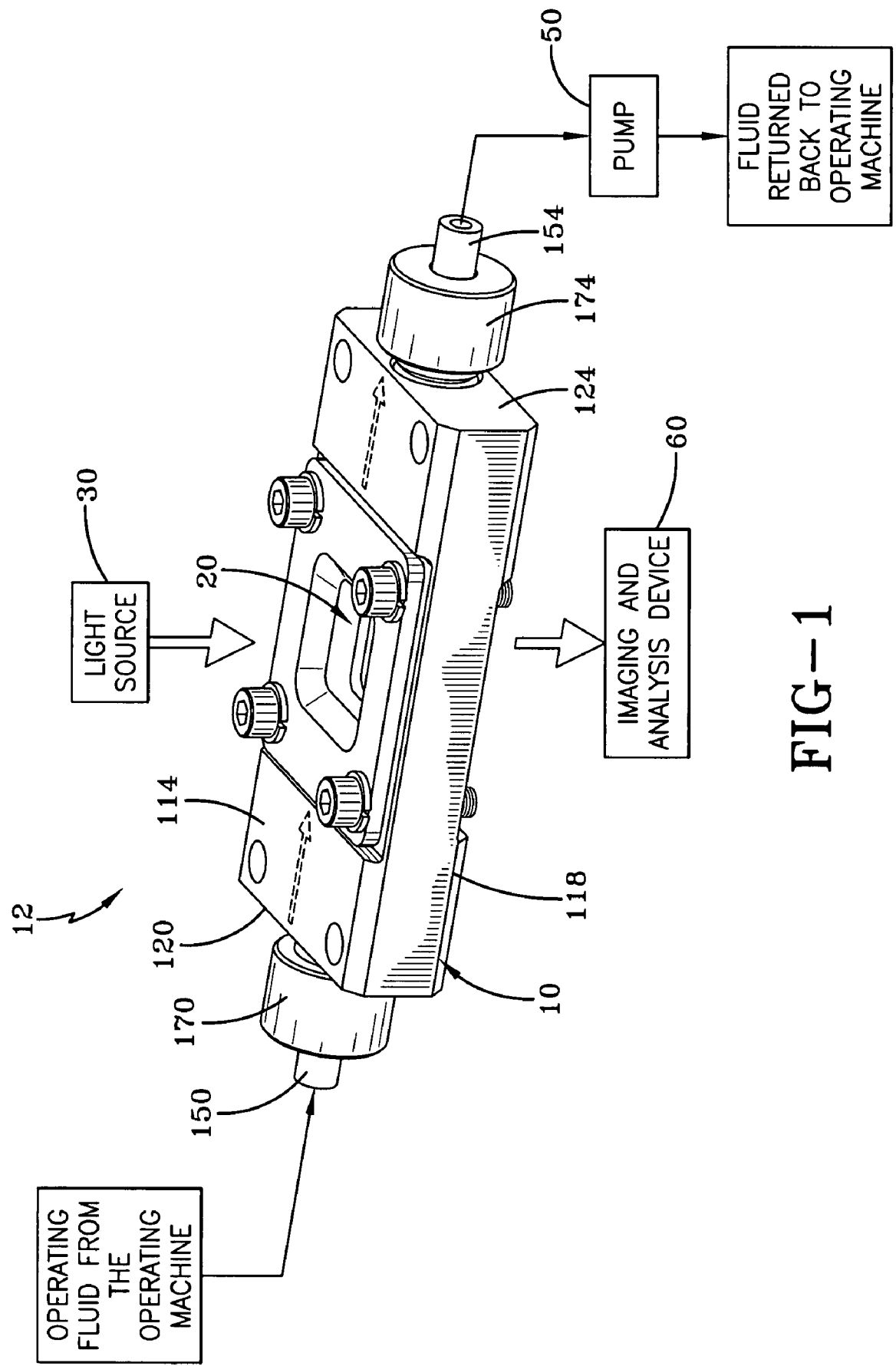
FIG. 1 is a block diagram showing an optical flow cell utilized with a fluid analysis system in accordance with the concepts of the present invention.

An online optical flow cell in accordance with the concepts of the present invention is generally referred to by the numeral 10 as shown in FIG. 1 of the drawings. Before discussing the particular aspects of the flow cell 10, a general overview of its operation will be set forth below. Furthermore, the term "operating fluid," as used herein, is defined as any fluid, including but not limited to lubricating fluid, hydraulic fluid, and liquid fuels, or the like. As such, it will be appreciated that any type of fluid could be passed through the optical flow cell described herein.

The flow cell 10 is generally utilized with a fluid analysis system 12 that includes several components that allows wear particles, or any other particle within a flow of operating fluid to be detected. To achieve such operation, the optical flow cell 10 maintains a transparent viewing area 20 that is configured to receive collimated light, such as a laser light, from a light source 30 maintained by the system 12. Operating fluid from an operating machine is drawn into the flow cell 10 via a flow delivery device, such as a pump 50. As the operating fluid enters the flow cell 10, the flow of operating fluid is modified to provide a laminar flow through the flow channel that passes through the viewing area 20. During this time, the light delivered from the light source 30 passes through the laminar flow within the transparent viewing area 20 and generates images that are detected by an imaging and analysis device 60. The images detected by the imaging and analysis device 60 are then analyzed to determine the particular shape of the wear particles that are suspended in the operating fluid. Once imaged, the operating fluid exits the flow cell 10 and returns to the operating machine. Thus, because the operating fluid within the flow cell 10 has a laminar flow, and because the flow cell 10 is configured to withstand elevated temperatures and/or pressures generated by the operating machine, the optical imaging system is able to achieve a more accurate and consistent identification of wear particles in such environments over prior art systems. As such, the flow cell 10 allows the optical imaging system to more accurately predict wear and generate predictive maintenance schedules in order to avoid operational delays that result when the operating machine is taken off-line or is otherwise made non-functional due to wear of its mechanical components. Thus, with the background of the operation of the flow cell 10 set forth, the specific structural aspects of the flow cell 10 will now be presented. It should also be appreciated that the optical flow cell 10 may be used with an optical imaging system, such as that discussed in U.S. patent application Ser. No. 11/228,172 to monitor operating fluid for a machine, such as an engine, although any other suitable imaging system may be utilized.

The flow cell 10 as discussed below is configured for online analysis of operating fluid maintained by an operating machine or other device, whereby the flow cell 10 is coupled directly thereto. Thus, the flow cell 10 is configured to receive a continuous sample of a portion of the aggregate operating fluid that is maintained by the operating machine or device. The continuous sample of operating fluid is analyzed, and then returned back to the aggregate supply. However, it should be appreciated that the flow cell 10 may be readily adapted for use in other manners, such as off-line and inline for example.

Figure 2:
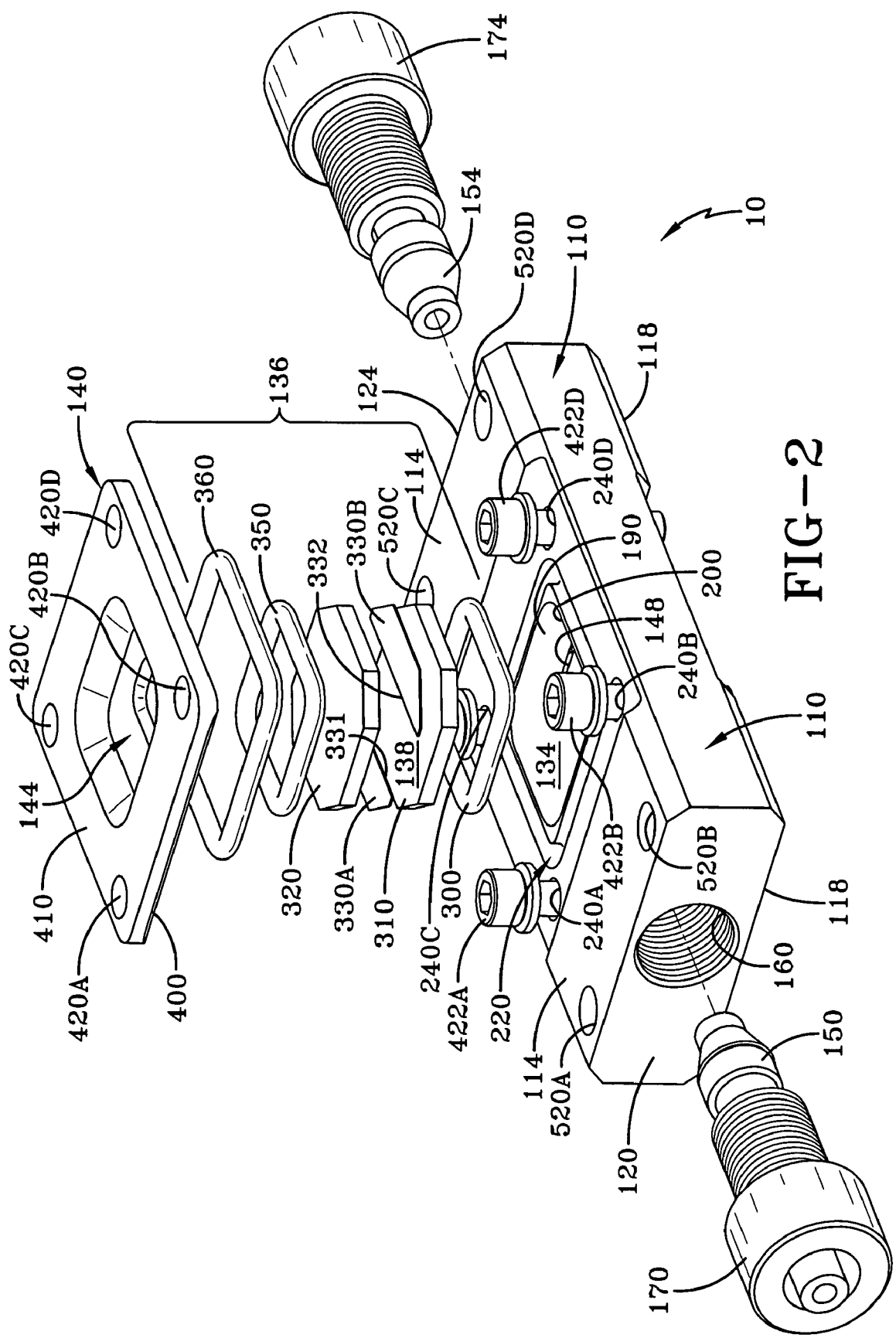
FIG. 2 is an exploded perspective view of an optical flow cell in accordance with the concepts of the present invention.
Figure 3:
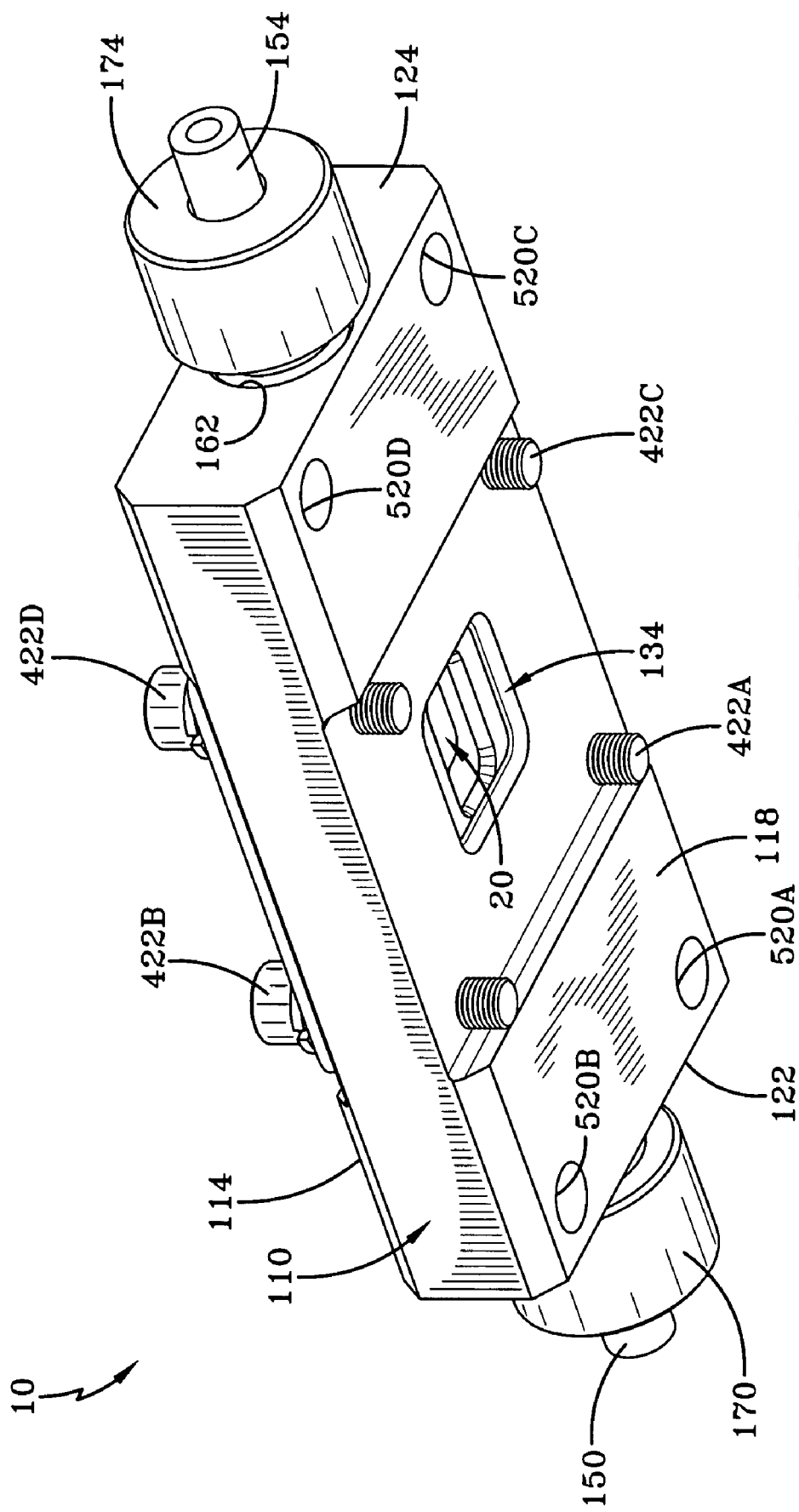
FIG. 3 is a bottom perspective view of the optical flow cell in accordance with the concepts of the present invention.
Figure 4:
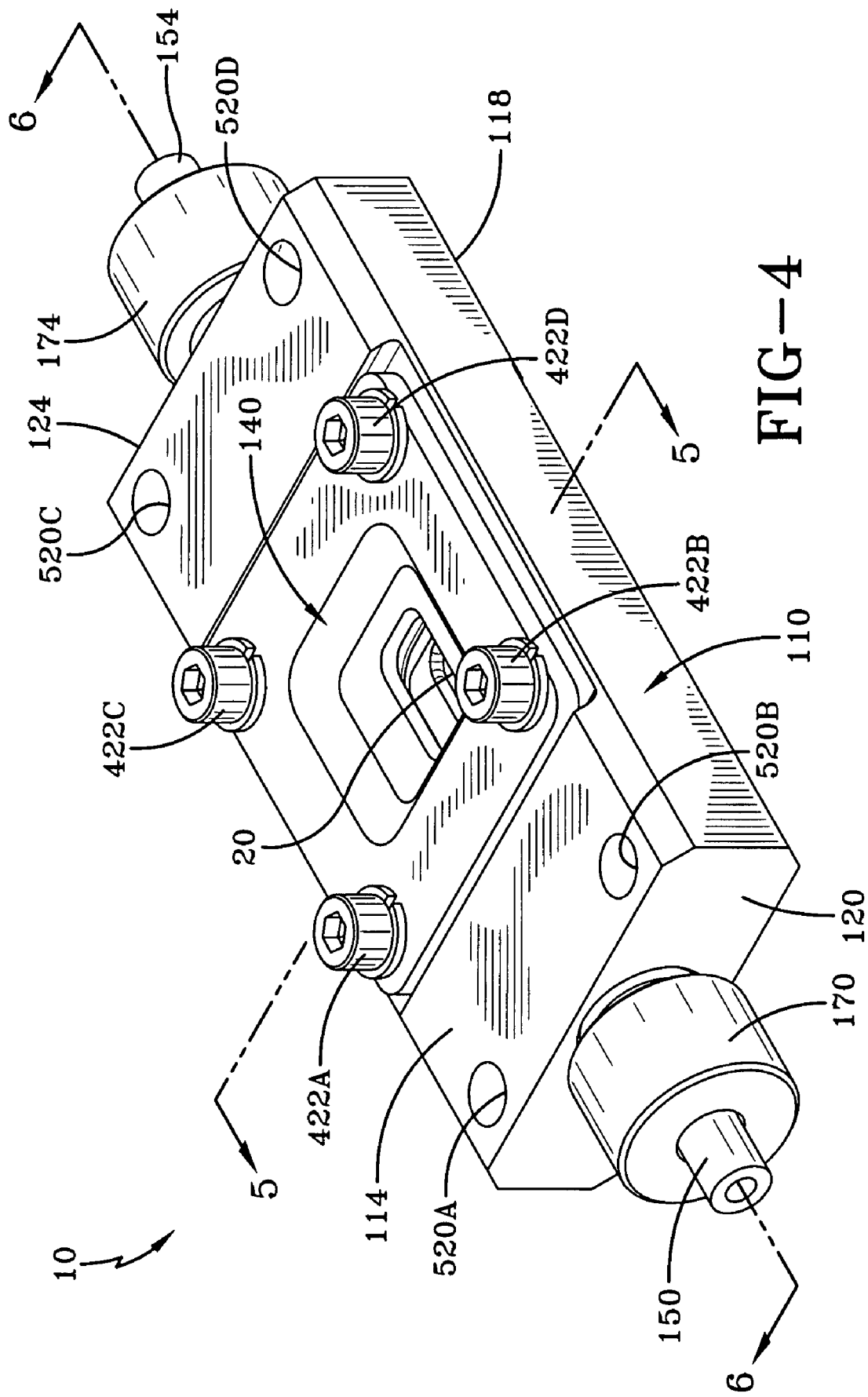
FIG. 4 is a perspective view of the optical flow cell with attached retainer in accordance with the concepts of the present invention.

As shown in FIGS. 2 and 3 the flow cell 10 comprises a body 110 having an outer surface 114 that is opposite a facing surface 118. The outer surface and facing surface 114,118 are connected by end surfaces 120 and 124 and corresponding side surfaces. It should be appreciated that the body 110 may be formed from stainless steel or any other material that is able to withstand environments with elevated temperatures and/or pressures. The body 110 includes a body aperture 134 therethrough, which enables light from the light source 30 to pass through during the operation of the flow cell 10. Within the body aperture 134 is disposed a flow channel assembly 136 that is retained therewithin by a retainer 140, which has a retainer aperture 144 that is aligned with the body aperture 134, when attached to the outer surface 114 of the body 110.

The flow channel assembly 136 comprises various components that coact to form a transparent flow channel 138. As will be discussed in more detail, the flow channel 138 is aligned with a pair of opposing flow slits 146,148 provided by the body 110. The body 110 has bores 160 and 162 in corresponding end surfaces 120 and 124. Operating fluid passes through the flow slits 146,148 and the flow channel 138 via inlet and outlet tubes 150 and 154 that are received and retained within respective bores 160 and 162 by respective threaded collars 170 and 174. Thus, during operation of the flow cell 10, the flow slits 146,148 and the flow channel 138 serve to impart a laminar flow to the operating fluid that enters the inlet tube 150 and exits the outlet tube 154. In addition, because the retainer aperture 144 and the body aperture 134 are aligned with each other, the imaging light from the fluid analysis system passes through the transparent flow channel 138.

Figure 5:
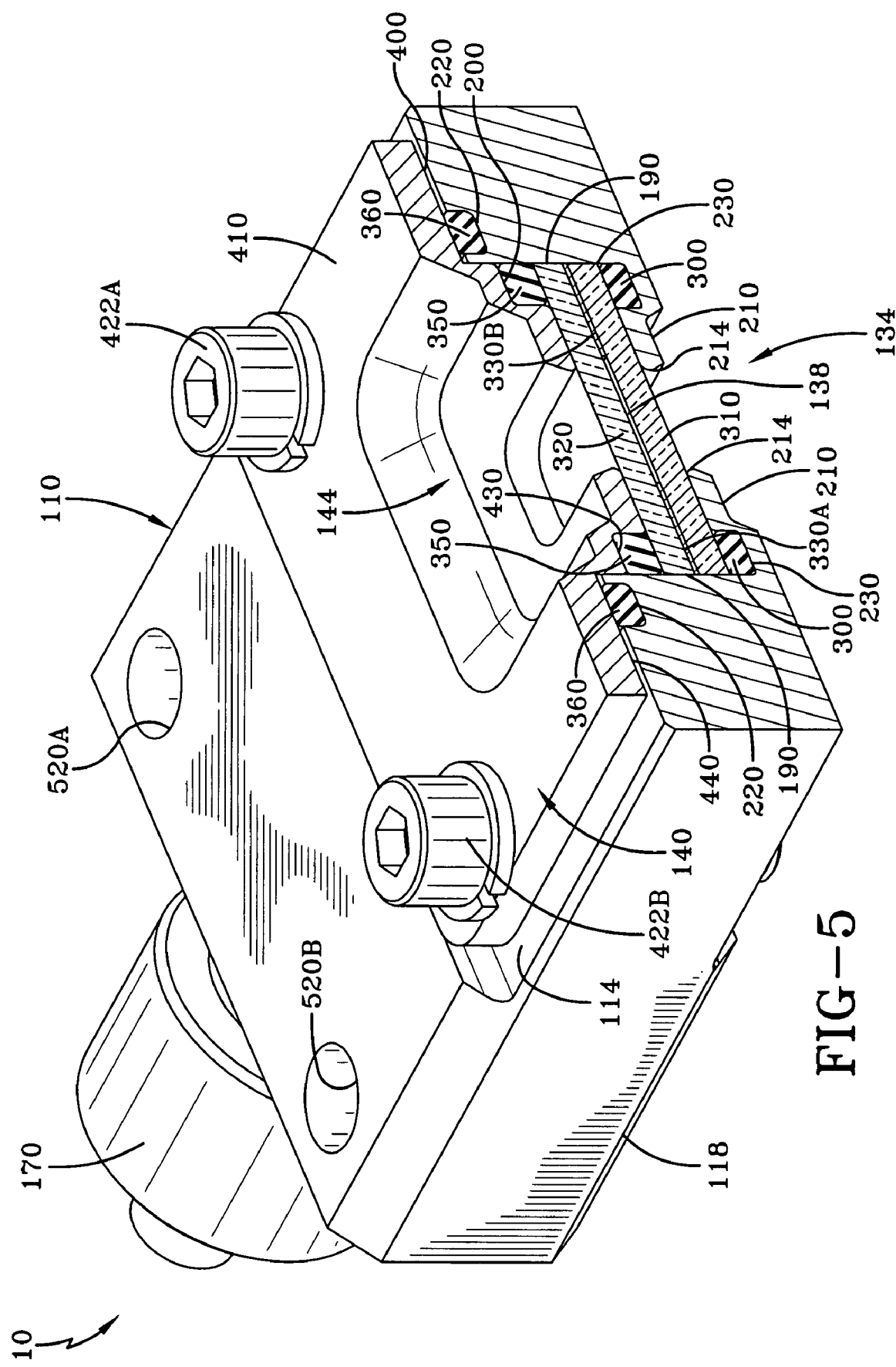
FIG. 5 is a perspective cross-sectional view of the optical flow cell in accordance with the concepts of the present invention.
Figure 6:
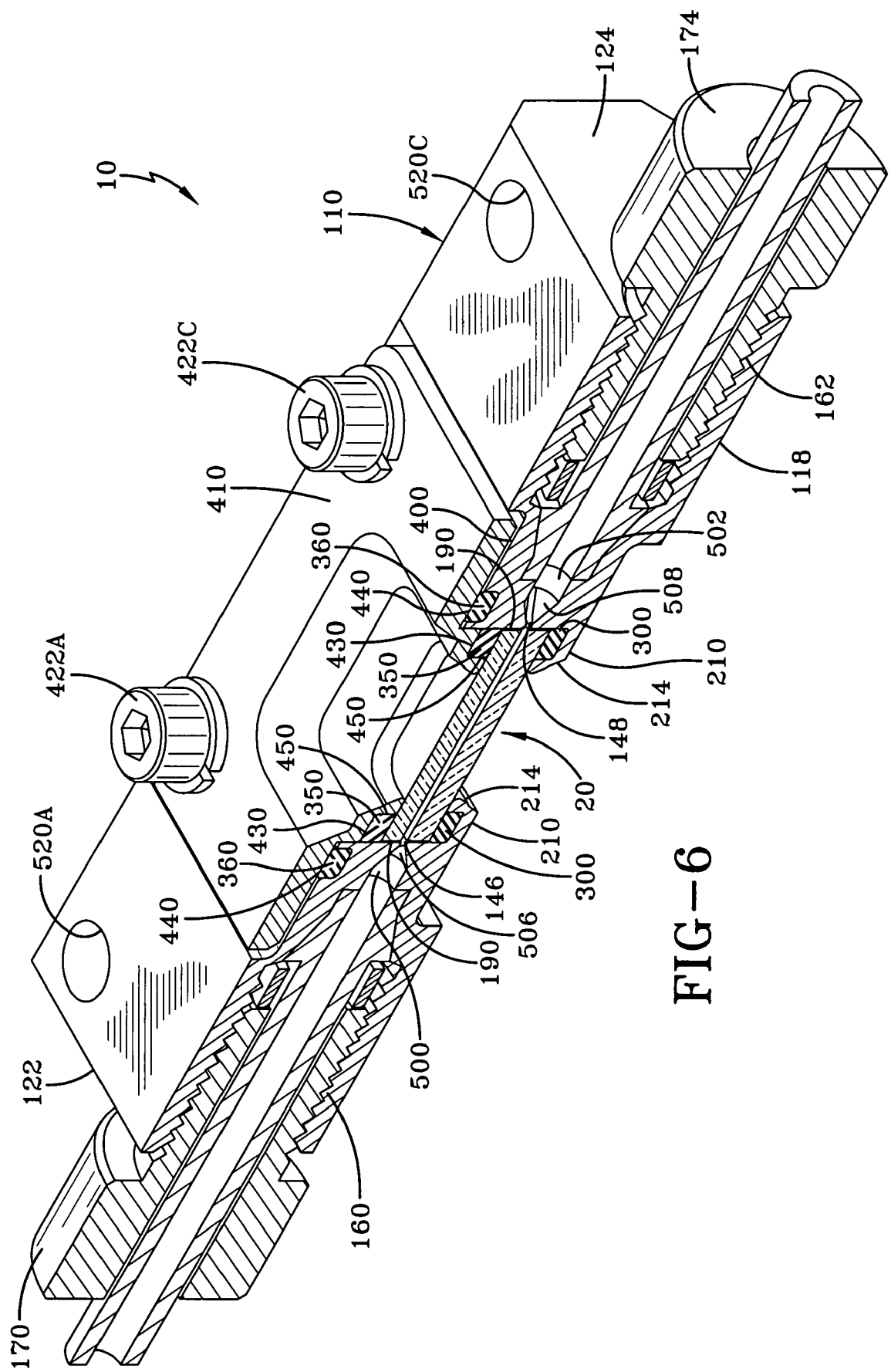
FIG. 6 is a perspective cross-sectional view of the optical flow cell in accordance with the concepts of the present invention.

As shown in the Figs, and more clearly in FIGS. 5 and 6, the body aperture 134 of the flow cell 10 includes a wall 190 having an upper edge 200 that is adjacent the outer surface 114 of the body 110. Within the body aperture 134 a support shelf 210 extends from the wall 190 forming a lower edge 214 that is adjacent the facing surface 118 of the body 110. Disposed about the periphery of the upper edge 200 is an outer channel 220, and arranged about the periphery of the lower edge 214, and recessed within the shelf 210 is an inner channel 230. Furthermore, disposed about the periphery of upper edge 200 are a plurality of threaded bores 240A-D that extend through the body 110 to facilitate the attachment of the retainer 140 discussed in detail below.

Figure 7:
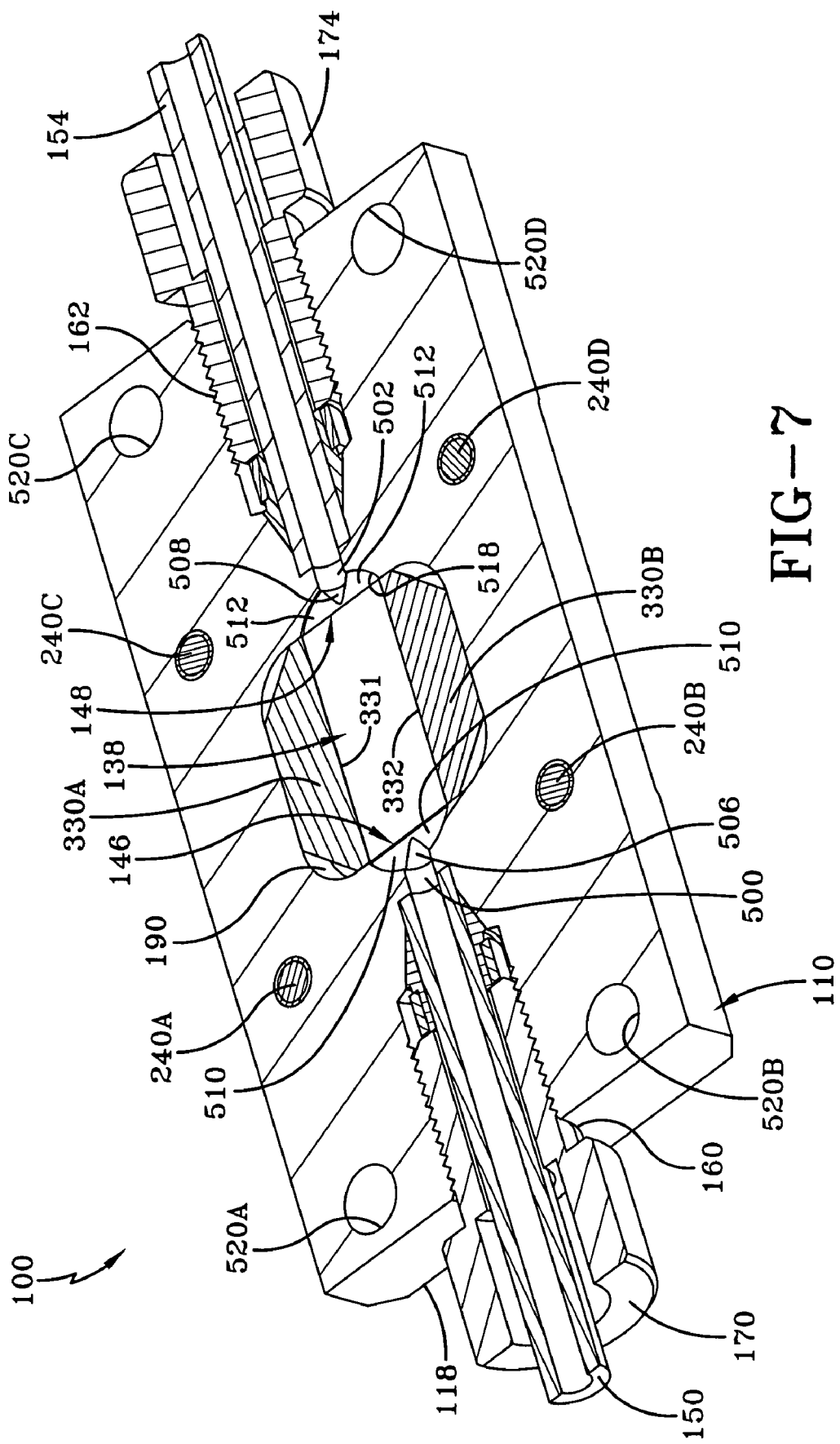
FIG. 7 is a perspective cross-sectional view of the optical flow cell in accordance with the concepts of the present invention.
Figure 8:
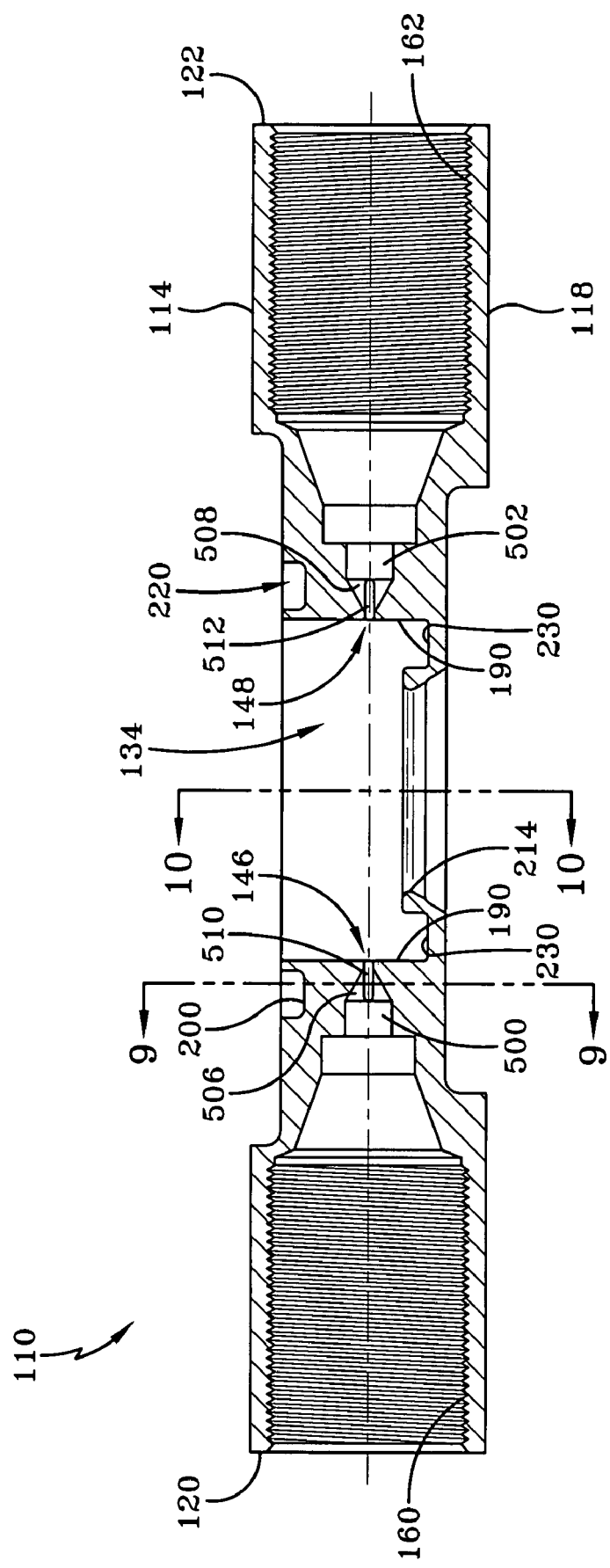
FIG. 8 is a cross-sectional view of the optical flow cell in accordance with the concepts of the present invention.
Figure 9:
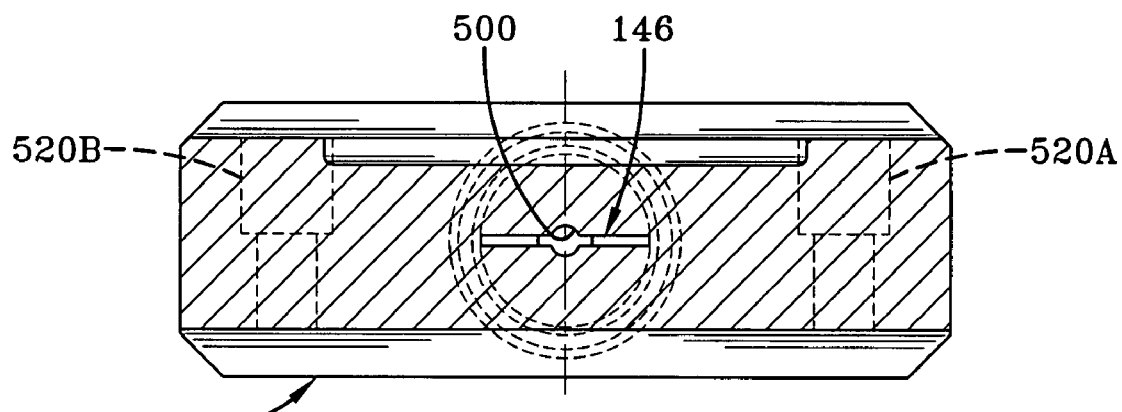
FIG. 9 is a cross-sectional view of the optical flow cell taken along line 9-9 in accordance with the concepts of the present invention.
Figure 10:
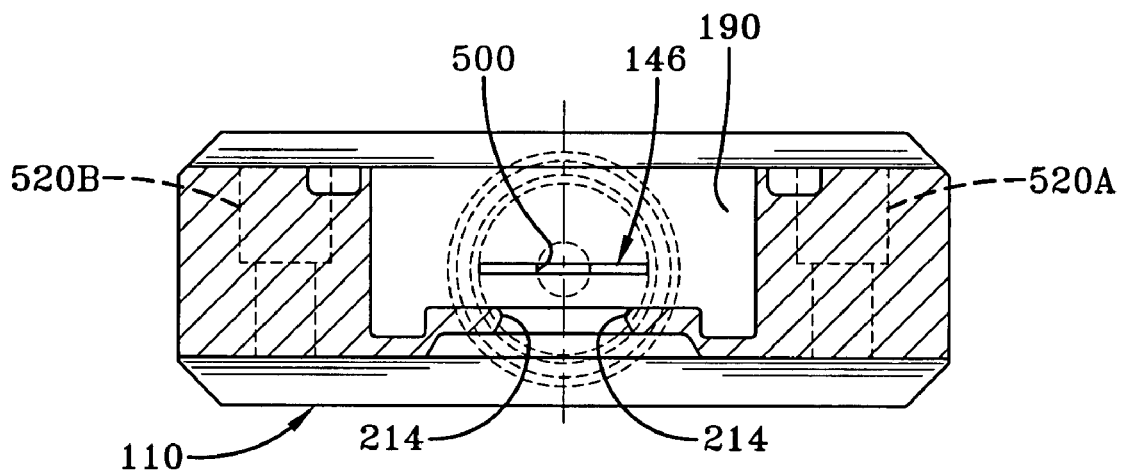
FIG. 10 is a cross-sectional view of the optical flow cell taken along line 10-10 in accordance with the concepts of the present invention.

Referring in particular to FIGS. 2, 4, 5, 6, and 7, disposed within the body aperture 134 of the flow cell 10 is the flow assembly 136. The flow assembly 136 comprises a lower seal 300 that is seated, or otherwise disposed within the inner channel 230. Disposed upon the lower seal 300 is a lower transparent plate 310, that is separated from an upper transparent plate 320 by a pair of laterally spaced shims 330A and 330B. The plates 310 and 320 may comprise transparent glass or any other suitable transparent material that is capable of withstanding operating environments having elevated temperatures and/or pressures. Similarly, the shims 330A-B may be formed from stainless steel, or any other material capable of withstanding environments with elevated temperatures and/or pressures. In addition to spacing the lower and upper plates 310,320 apart, the shims 330A-B are arranged so that their respective facing edges 331 and 332 are spaced apart at a distance that matches the width dimension of the slits 146 and 148. Referring to FIG. 7, as well as to the other Figs., it should be appreciated that the height dimension of the shims 330A-B substantially matches the height dimension of the slits 146,148, so as to allow the flow channel 138 to be substantially aligned with the inlet and outlet slits 146,148. As such, the spaced plates 310,320 define the height of the flow cell 138, while the spaced edges 331 and 332 of the spaced shims 330A-B define the width of the flow channel 20. In other words, the edges 331,332 of the shims 330A-B are aligned with the vertical edges of the slits 146,148, while the lower and upper plates 310,320 are aligned with the respective lower and upper horizontal edges of the slits 146,148.

Continuing, disposed upon the upper plate 320 is an upper seal 350 that is dimensioned to be adjacent the wall 190, below the upper edge 200 of the body aperture 134. Finally, the flow channel assembly 136 includes an external seal 360 that is disposed within the outer channel 220. It should be appreciated that the seals 300, 350, and 360 may comprise rubber seals or any other suitable sealing means. In order to retain the plates 310,320, the shims 330A-B, and to provide a sufficient compressive force to the seals 300,350,360 so as to form a liquid tight seal about the flow channel 138, the retainer 140 is attached to the body 110 of the flow cell 10 in the manner to be discussed.

The retainer 140 provides inner and outer surfaces 400 and 410 through which a plurality of attachment bores 420A-D pass. As shown in FIG. 2, the attachment bores 420A-D allow the retainer 140 to be attached to the body 110 by fasteners 422A-D received therethrough, which are received by the threaded bores 240A-D maintained by the body 110. It should be appreciated, that the fasteners 422A-D may be comprised of stainless steel, although any other suitable material may be used. On its inner surface 400, the retainer 140 maintains inner and outer concentrically arranged compression steps 430 and 440. The inner and outer compression steps 430,440 are configured to respectively provide a direct compressive force to the upper seal 350 and external seal 360. Further, a lateral step 450 provides a lateral force to the upper seal 350 to ensure that it forms a seal against the wall 190 of the body aperture 134. In addition, the retainer 140 provides indirect compressive force to the lower seal 300, as well as to the plates 310,320 and shims 330A-B to assist in retaining them in place.

Figure 11:
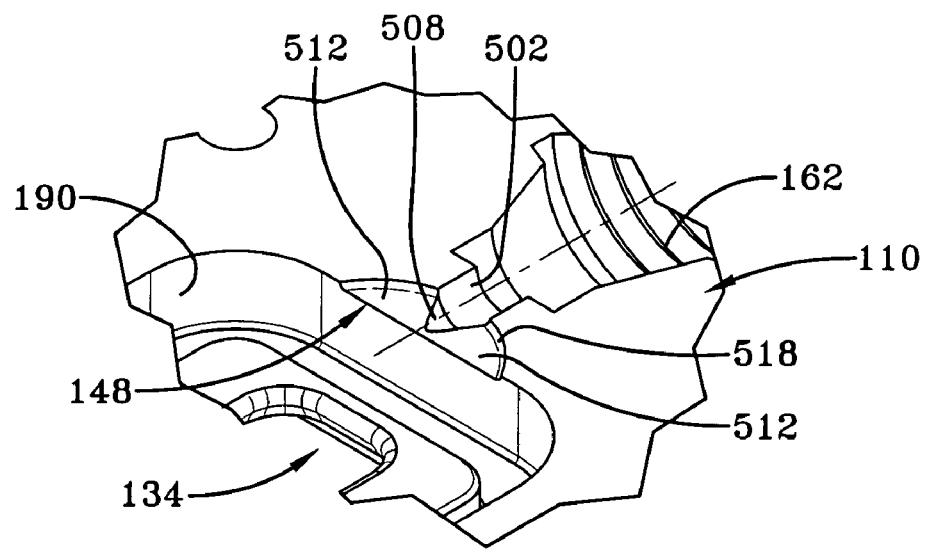
FIG. 11 is a perspective view of the optical flow cell showing a flow slit in accordance with the concepts of the present invention.

In addition, the body 110 also includes threaded bores 160,162, which are disposed at each end surface 120 and 124 of the body 110 of the flow cell 10. The threaded retainers 170,174 are threadably received within the bores 160,162 to retain the inlet and outlet tubes 150,154 therein. As such, the inlet tube 150 carries operating fluid to the flow channel 20, while the outlet tube 154 carries the operating fluid away from the flow channel 20. However, it should be appreciated that either end 124 of the flow cell 10 may serve as an inlet or outlet of operating fluid. Furthermore, the bores 160,162 extend within the body 110 of the flow cell 10, with their cross-sectional shape transitioning to a nozzle end 500,502 having a somewhat cylindrical shape. Coaxial with the nozzle end 500,502 is a somewhat conical nozzle transition 506,508 that transitions to a transition flow area 510,512. The transition flow area 510,512 is comprised of a substantially flat surface that is defined by a radiused wall 516,518 and the wall 190 within the body aperture 134. It should be appreciated, that the radiused wall 516,518 are not required to be radially dimensioned as shown in FIG. 11, and may take on any desired profile or dimension. As such, the nozzle end 500, 502, the nozzle transition 506,508, and the transition flow are 510,512 fluidly communicate so as to condition the operating fluid before it passes into the rectangular flow slits 146,148 that are disposed within the wall 190 of the body aperture 134.

The rectangular cross-section of the flow slits 146,148, and the rectangular cross-section of the flow channel 20 contributes to the laminar flow imparted to the operating fluid as it passes through the viewing area 20. In addition, the flow cell 10 may include one or more mounting bores 520A-D, configured to receive a suitable fastener therethrough, for mounting the flow cell 10 in a desired location.

Due to the configuration of the flow cell 10, and its ability to be manufactured at a reduced size, it can be used to monitor operating fluid in confined areas and in environments which have elevated temperatures and/or pressures. For example, the flow cell 10 may be used in environments having a pressure of up to about 400 psi (pounds per square inch) and temperatures in the range of −40 degrees Celsius to 120 degrees Celsius, although such should not be construed as limiting as the flow cell 10 may be utilized in environments with other pressure and/or temperature ranges.

The flow cell 10 is able to achieve its operational performance in high temperature and/or high-pressure environments, while maintaining the integrity of the glass plates 310 and 320 that define the flow channel 138, due at least in part to the particular selection of materials used to form the flow channel 138. That is, the selection of the particular materials utilized to comprise the body 110, the retainer 140, the shims 330A-B, and the fasteners 422A-D allow the flow cell 10 to retain its ability to provide a laminar flow of operating fluid through the flow channel 138 at elevated pressures and/or temperatures. As such, the materials comprising the body 110, the retainer 140, the shims 330A-B, and the fasteners 422A-D are selected so that the thermal expansion coefficients of those materials used complement each other, so as to prevent any rupture or failure of the flow channel 138 as the environmental temperatures and/or pressures to which the flow cell 10 is subjected vary.

During operation of the flow cell 10, operating fluid from the engine, operating machine, or other device utilizing the operating fluid is drawn into the flow cell 10 by the inlet tube 150, via the pump 50 or other means that is operatively coupled to the outlet tube 154. In addition, the light source 30 maintained by the fluid analysis system 12 is positioned proximate the outer surface 114, and directs a light beam, such as a laser, though the transparent flow channel 20. On the other side of the flow cell 10 proximate the facing surface 118, is the imaging and analysis device 60 that is arranged so as to receive the light passing through the flow channel 20. As the operating fluid is received from the inlet tube 150, it is channeled through the nozzle 500, into the inlet flow slit 146, and into the flow channel 20. The inlet flow slit 146, flow channel 20, and the outlet flow slit 148 serves to take the flow of the operating fluid, which may be characterized by turbulence, and normalizes it into a laminar flow that is generally devoid of turbulence and other disturbances. The light passing through the laminar flow of operating fluid forms an imaging signal detected by the imaging and analysis device 60 that represents the various wear particles suspended within the operating fluid. In addition, the laminar flow of the operating fluid through the flow channel 20 allows any wear particles suspended in the operating fluid to be oriented in a consistent manner so that the characteristic shape of the wear particle can be determined by the fluid analysis system 12. As such, the fluid analysis system 12 is able to more accurately predict the level of wear being experienced by the engine or other mechanical machine. Finally, once the operating fluid passes through the flow chamber 20, it exits through the outlet tube 154 via the outlet flow slit 148.

It will, therefore, be appreciated that one advantage of one or more embodiments of the present invention is that a flow cell may be used to impart a laminar flow to operating fluid as it passes through a flow channel. Still another advantage of the present invention is that the flow cell may operate in environments with elevated temperatures and/or pressures. Yet another advantage of the present invention is that wear particles within the operating fluid passing through the flow channel are oriented more consistently so that the shape of the wear particle can be characterized more accurately by an imaging system.

Although the present invention has been described in considerable detail with reference to certain embodiments, other embodiments are possible. Therefore, the spirit and scope of the appended claims should not be limited to the description of the embodiments contained herein.

What is claimed is:

1. A flow cell to monitor particles in a fluid comprising:
   a body having a body aperture therethough forming a wall surface;
   an inlet slit and an outlet slit integral with opposing sides of said wall surface,
   a flat transition flow area in fluid communication with each said slit, each said flat transition flow area maintaining an at least partial conical nozzle transition disposed therein, said flat transition flow area and said at least partial conical nozzle transition integral with said body;
   a pair of spaced transparent plates disposed within said aperture, the space between said plates defining a flow channel substantially aligned with each of said slits allowing the fluid to pass therethrough in a laminar manner; and
   a retainer attached to said body to retain said plates in place, said retainer having a retainer aperture, wherein said body aperture, said flow channel, and said retainer aperture are substantially aligned to allow light to pass therethrough,
   wherein incoming fluid is received by said flat transition flow area and said at least partial conical nozzle transition before entering said inlet slit to form a laminar flow of fluid that passes through said flow channel to said outlet slit.

2. The flow cell of claim 1, wherein said plates are formed from glass.

3. The flow cell of claim 1, wherein said flow channel is configured to withstand temperatures in the range of about −40 degrees Celsius to 120 degrees Celsius.

4. The flow cell of claim 1, wherein said flow channel is configured to withstand pressures up to about 400 psi.

5. The flow cell of claim 1, wherein said body is formed from stainless steel.

6. The flow cell of claim 1, wherein said retainer is formed from stainless steel.

7. The flow cell of claim 1, further comprising a pair of spaced shims disposed between said plates.

8. The flow cell of claim 7, wherein each of said shims includes an edge that is aligned with the vertical edges of each of said slits.

9. The flow cell of claim 8, wherein one of said plates is aligned with the upper horizontal edge of said slits, and another of said plates is aligned with the lower horizontal edge of said slits.

10. The flow cell of claim 7, wherein said shims are formed from stainless steel.

11. The flow cell of claim 1, wherein said retainer is attached to said body by at least one stainless steel fastener.

12. The flow cell of claim 1, further comprising a pair of bores disposed within opposing ends of said body, each said bore coupled to one said slit, whereby said bore associated with said inlet slit allows the flow of the fluid into said flow channel, and said bore associated with said outlet slit allows the flow of fluid out of said flow channel.

13. The flow cell of claim 1, wherein said transition flow area is defined by a radiused wall and said wall surface.

14. The flow cell of claim 1, further comprising a nozzle end that is disposed within said body and in fluid communication with each said nozzle transition.

15. The flow cell of claim 14, wherein said nozzle end is substantially cylindrical.

16. The flow cell of claim 1, wherein said wall surface maintains an upper edge opposite a lower edge, whereby extending from said lower edge toward said body aperture is a support shelf upon which said transparent plates are supported.

17. The flow cell of claim 16, wherein said support shelf includes an inner 2 channel disposed about its periphery, said inner channel maintaining a first o-ring.

18. The flow cell of claim 17, wherein one of said plates is positioned adjacent said first o-ring disposed in said inner channel, while a second o-ring is disposed between said retainer and the other said plate.

19. A flow cell to monitor particles in a fluid comprising:
   a body having a body aperture therethrough forming a wall surface;
   a pair of slits disposed within opposing sides of said wall surface, wherein one of said slits receives an incoming flow of fluid, and the other slit receives an outgoing flow of fluid;
   a pair of spaced transparent plates disposed within said aperture, the space between said plates defining a flow channel substantially aligned with each of said slits allowing the fluid to pass therethrough in a laminar manner;
   a retainer attached to said body to retain said plates in place, said retainer having a retainer aperture, wherein said body aperture, said flow channel, and said retainer aperture are substantially aligned to allow light to pass therethrough, wherein said wall surface maintains an upper edge opposite a lower edge, whereby extending from said lower edge toward said body aperture is a support shelf upon which said transparent plates are supported;
   said support shelf includes an inner channel disposed about its periphery, said inner channel maintaining a first o-ring, wherein one of said plates is positioned adjacent said first o-ring disposed in said inner channel, while a second o-ring is disposed between said retainer and the other said plate; and
   an outer channel disposed about the periphery of said upper edge of said wall surface, wherein said outer channel carries a third o-ring that is adjacent said retainer.

20. The flow cell of claim 19, wherein said retainer includes inner and outer compression steps, said inner step configured to contact said second o-ring, and said outer step configured to contact said third o-ring.

21. The flow cell of claim 20, wherein said retainer further comprises a lateral step that extends from said inner step toward said lower edge of said body, said lateral step configured to contact said second o-ring.

* * * * *